(12) United States Patent
Zalevsky et al.

(10) Patent No.: US 11,284,786 B2
(45) Date of Patent: Mar. 29, 2022

(54) SPATIAL ENCODING SYSTEM DECODING SYSTEM IMAGING SYSTEM AND METHODS THEREOF

(71) Applicant: ZSquare Ltd., Petah Tikva (IL)

(72) Inventors: Zeev Zalevsky, Rosh-HaAyin (IL); Omer Itzchak Wagner, Rosh-HaAyin (IL); Asaf Shahmoon, Petah-Tikva (IL)

(73) Assignee: ZSquare Ltd., Petah Tikva (IL)

( * ) Notice: Subject to any disclaimer, the term of this patent is extended or adjusted under 35 U.S.C. 154(b) by 0 days.

(21) Appl. No.: 16/296,165

(22) Filed: Mar. 7, 2019

(65) Prior Publication Data
US 2020/0281451 A1    Sep. 10, 2020

(51) Int. Cl.
| | |
|---|---|
| *A61B 1/06* | (2006.01) |
| *G02B 27/42* | (2006.01) |
| *H04N 5/238* | (2006.01) |
| *A61B 1/05* | (2006.01) |
| *A61B 1/00* | (2006.01) |
| *H04N 5/225* | (2006.01) |

(52) U.S. Cl.
CPC ........ *A61B 1/0638* (2013.01); *A61B 1/00172* (2013.01); *A61B 1/05* (2013.01); *A61B 1/063* (2013.01); *G02B 27/4205* (2013.01); *H04N 5/2256* (2013.01); *H04N 5/238* (2013.01); *H04N 2005/2255* (2013.01)

(58) Field of Classification Search
CPC combination set(s) only.
See application file for complete search history.

(56) References Cited

U.S. PATENT DOCUMENTS

| | | | |
|---|---|---|---|
| 6,485,413 B1 * | 11/2002 | Boppart | A61B 1/00096 |
| | | | 356/450 |
| 9,080,899 B2 | 7/2015 | Tobiason | |
| 2015/0238276 A1 * | 8/2015 | Atarot | A61B 1/00004 |
| | | | 600/424 |
| 2016/0309068 A1 * | 10/2016 | Nadeau | A61B 5/1455 |
| 2018/0110422 A1 * | 4/2018 | Nakao | A61B 1/00167 |
| 2018/0367742 A1 * | 12/2018 | Ando | H04N 5/2254 |

(Continued)

OTHER PUBLICATIONS

Wagner et al., Superresolved imaging based on wavelength multiplexing of projected unknown speckle patterns, OSA Publishing, Applied Optics, vol. 54, Issue 13, Pages D51-D60 (Year: 2015).*

(Continued)

*Primary Examiner* — Christopher S Kelley
*Assistant Examiner* — Asmamaw G Tarko
(74) *Attorney, Agent, or Firm* — Pearl Cohen Zedek Latzer Baratz LLP

(57) ABSTRACT

A system for imaging may include an illumination system that includes a light source to generate a light beam; and a spatial encoding pattern generator comprising one or a plurality of optical elements to encode the imaging beam so as to concurrently illuminate an object by a plurality of different spatial encoding patterns, wherein each encoding pattern of said different encoding patterns is characterized by a distinct wavelength of the imaging pattern. The system may also include an imaging sensor for receiving the encoded imaging beam transmitted through the object or reflected off the object; and a processor for decoding image data from the imaging and reconstructing an image of the object.

16 Claims, 8 Drawing Sheets

(56) References Cited

U.S. PATENT DOCUMENTS

| 2019/0028641 A1* | 1/2019 | Rigneault | H04N 5/23232 |
| 2019/0049896 A1* | 2/2019 | Cheng | G03H 1/0443 |
| 2019/0150751 A1* | 5/2019 | Yang | A61B 5/0042 |
| 2019/0219509 A1* | 7/2019 | Lo | G01N 15/147 |
| 2020/0110026 A1* | 4/2020 | Choi | G03H 1/0443 |

OTHER PUBLICATIONS

Wagner et al. "Superresolved imaging based on wavelength multiplexing of projected unknown speckle patterns," Appl. Opt. 54, D51-D60 (2015) May 1, 2015.

Mico et al., "Single-step superresolution by interferometric imaging," Optics Express vol. 12, No. 12, pp. 2589-2596 ; Jun. 14, 2004; available at URL https://www.osapublishing.org.

Dorozynska et al. "Implementation of a multiplexed structured illumination method to achieve snapshot multispectral imaging," Optics Express vol. 25, No. 5, pp. 17211-17226, Jul. 24, 2017.

International Search Report and Written Opinion for PCT Application No. PCT/IL2020/050257, dated May 25, 2020.

\* cited by examiner

SPATIAL ENCODING SYSTEM DECODING SYSTEM IMAGING SYSTEM AND METHODS THEREOF

FIELD OF THE INVENTION

The present invention relates to imaging. More specifically, the present invention relates to spatial encoding system, decoding system, imaging system and methods thereof.

BACKGROUND OF THE INVENTION

In-vivo biological tissue imaging typically requires careful choosing between different bio-imaging methods befitting the specific experimental requirements and conditions. Deep penetrating non-invasive imaging techniques such as magnetic resonance imaging (MRI), computed tomography (CT), high and low frequency ultrasound (US) are expensive, limited in duration and in spatial resolution. Other high-resolution approaches like single/multiple photon fluorescence or confocal fluorescence micro-endoscopy can be used in-vivo but are typically only useful in shallow interrogation depths.

Micro-endoscopes optical fibers have been developed to be deeply inserted, in minimally invasive techniques, into the target area within a patient's body. Such devices enable a long-term, in-vivo monitoring of the biological sample. Many commercial micro-endoscopes optical fibers include numerous core-bundles, known as multicore fibers (MCF), where each core acts as a single fiber.

Many MCF include multimode fibers (MMF) that allow passing of many spatial electromagnetic modes through each core, thus increasing intensity transmittance of an image through the endoscope. However, MMF typically scramble the information transmitted through them both in space and time. This problem may be addressed by MCF designs that have large-enough spaces between neighboring cores to minimize core-to-core light coupling (cross-talk). As a result, image resolution may be damaged and pixelization artifacts may appear in the generated image. Other solutions such as optimization algorithms, digital phase conjugation or transmission matrix were demonstrated, but are all typically sensitive to fiber bending.

Single mode fiber bundles (SMFB), which are typically less sensitive to the fiber bending and less prone to information scramble, may be used, instead of MMF. SMFB imaging typically includes employing scanning heads with lenses, a spectral disperser, speckle correlations and may also involve other techniques, which may yield resolutions up to the diffraction limit. While the SMFB core-to-core length may be reduced, the brightness of the image transmitted through the device may also be reduced. Consequentially, the signal to noise ratio may be reduced as well. Along with the necessary geometrical design of the fiber, the resolution may still be limited and the depth of viewing through scattering medium may be greatly degraded too.

In both MMF and SMFB bundles, various illumination methods through the fiber are known, for example, illumination of the sample and collection of reflected light through the same bundle, confocal micro-endoscopes which can perform optical sectioning, speckle correlation techniques that are able to conduct optical sectioning without staining and others.

Current technologies exhibit a typical penetration depth of less than 150 μm and have difficulties in dealing with real biological scattering media (e.g., blood) between the distal end of the fiber and the sample. Also, typical imaging acquisition rate is rather poor (typically, roughly between 5 Hz for a 36×36 pixel image up to several minutes).

SUMMARY OF THE INVENTION

There is thus provided, according to some embodiments of the present invention, an illumination system that includes a light source to generate a light beam and a spatial encoding pattern generator comprising one or a plurality of optical elements to encode the imaging beam so as to concurrently illuminate an object by a plurality of different spatial encoding patterns, wherein each encoding pattern of said different encoding patterns is characterized by a distinct wavelength of the imaging pattern.

In some embodiments of the invention, the system also includes one or more optical elements to split the light beam into an imaging beam and a reference beam and direct the reference beam to the imaging sensor after the reference beam is combined with the imaging beam.

In some embodiments of the invention, the spatial encoding pattern generator is configured to image said plurality of different spatial encoding patterns onto the object across a first axis that is perpendicular to a direction of propagation the imaging beam and configured to perform a Fourier transform of said plurality of different spatial encoding patterns onto the object across a second axis that is both perpendicular to the first axis and to the direction of propagation of the imaging beam.

In some embodiments of the invention, the one or a plurality of optical elements to encode the imaging beam are aligned along an optical path in the following order: a diffraction grating grid, a first lens, an encoding pattern element, and a second lens.

In some embodiments of the invention, the first lens is distanced from the diffraction grating grid and from the encoding pattern element by a distance equal to an X-axis focal length of the first lens, and wherein the second lens is distanced from the encoding pattern element by a distance equal to an X-axis focal length of the second lens.

In some embodiments of the invention, an X-axis focal length of each of the lenses is twice a Y-axis focal length of that lens.

In some embodiments of the invention, said one or a plurality of optical elements to encode the imaging beam define the optical path comprising, in the following order, the diffraction grating grid, the first lens, the encoding pattern element, the second lens, a second diffraction grating grid, and a third lens.

In some embodiments of the invention, the first lens is distanced from the diffraction grating grid and from the encoding pattern element by a distance equal to an X-axis focal length of the first lens, wherein the second lens is distanced from the encoding pattern element by a distance equal to an X-axis focal length of the second lens, and wherein the third lens is distanced from the second diffraction grating grid by a distance equal to an X-axis focal length of the third lens.

In some embodiments of the invention, an X-axis focal length of each of the lenses is twice a Y-axis focal length of that lens.

In some embodiments of the invention, the light source is a laser generator.

In some embodiments of the invention, the laser source is a pulsed laser source.

In some embodiments of the invention, the system is incorporated in an endoscope.

In some embodiments of the invention, the system is incorporated in an imaging system, the imaging system further including an imaging sensor for receiving the encoded imaging beam transmitted through the object or reflected off the object; and a processor for decoding image data from the imaging and reconstructing an image of the object.

In some embodiments of the invention, for reconstructing the image of the object, the processor is configured to multiply an image of each encoding pattern of said different encoding patterns that is obtained from the reflected or transmitted encoded imaging beam, by a corresponding decoding pattern to obtain a product and to sum all of the products to obtain the reconstructed image of the object.

In some embodiments of the invention, there is provided a decoding system that includes an imaging sensor for receiving an encoded imaging beam that concurrently illuminated an object by a plurality of different spatial encoding patterns, wherein each encoding pattern of said different encoding patterns is characterized by a distinct wavelength of the imaging pattern, and that was transmitted through the object or reflected off the object. The decoding system also includes a processor for decoding image data from the imaging and reconstructing an image of the object.

In some embodiments of the invention, for reconstructing the image of the object, the processor is configured to multiply an image of each encoding pattern of said different encoding patterns, that is obtained from the reflected or transmitted encoded imaging beam, by a corresponding decoding pattern to obtain a product and to sum all of the products to obtain the reconstructed image of the object.

In some embodiments of the invention, there is provided a method that includes generating a light beam; and using a spatial encoding pattern generator, encoding the imaging beam so as to concurrently illuminate an object by a plurality of different spatial encoding patterns, wherein each encoding pattern of said different encoding patterns is characterized by a distinct wavelength of the imaging pattern.

In some embodiments of the invention, the encoding the imaging beam comprises applying temporal gating.

In some embodiments of the invention, the temporal gating is applied using any of the techniques of the technique group consisting of short light pulses gating, coherence gating and interference pattern generated by a diffraction grating grid.

In some embodiments of the invention, the spatial encoding pattern generator comprises one or a plurality of optical elements to encode the imaging beam, which are aligned along an optical path in the following order: a diffraction grating grid, a first lens, an encoding pattern element, and a second lens.

In some embodiments of the invention, the encoding of the imaging beam comprises applying temporal gating wherein the temporal gating is realized by splitting the light beam into an imaging beam and a reference beam and directing the reference beam to the imaging sensor after the reference beam is combined with the imaging beam.

In some embodiments of the invention, there is provided a method that includes using an imaging sensor, receiving an encoded imaging beam that concurrently illuminated an object by a plurality of different spatial encoding patterns, wherein each encoding pattern of said different encoding patterns is characterized by a distinct wavelength of the imaging pattern, and that was transmitted through the object or reflected off the object; and using a processor, decoding image data from the imaging and reconstructing an image of the object.

BRIEF DESCRIPTION OF THE DRAWINGS

In order the present invention to be better understood and its practical applications appreciated, the following figures are provided and referenced hereafter. It should be noted that the figures are given as examples only and in no way limit the scope of the invention. Like components are denoted by like reference numerals.

DETAILED DESCRIPTION OF THE INVENTION

Figure 1A:
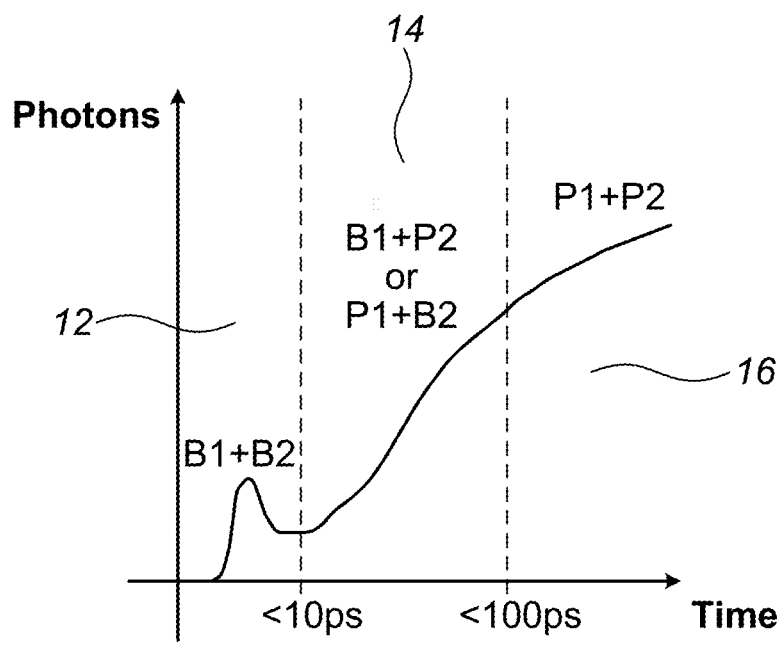
FIG. 1A is a graph showing photon count vs. time for interaction of light with scattering medium.

In the following detailed description, numerous specific details are set forth in order to provide a thorough understanding of the methods and systems. However, it will be understood by those skilled in the art that the present methods and systems may be practiced without these specific details. In other instances, well-known methods, procedures, and components have not been described in detail so as not to obscure the present methods and systems.

Although the examples disclosed and discussed herein are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. Unless explicitly stated, the method examples described herein are not constrained to a particular order or sequence. Additionally, some of the described method examples or elements thereof can occur or be performed at the same point in time.

Unless specifically stated otherwise, as apparent from the following discussions, it is appreciated that throughout the specification, discussions utilizing terms such as "adding", "associating" "selecting," "evaluating," "processing," "computing," "calculating," "determining," "designating," "allocating" or the like, refer to the actions and/or processes of a computer, computer processor or computing system, or similar electronic computing device, that manipulate, execute and/or transform data represented as physical, such as electronic, quantities within the computing system's registers and/or memories into other data similarly represented as physical quantities within the computing system's memories, registers or other such information storage, transmission or display devices.

According to some embodiments of the present invention, a novel optical setup is provided, aimed at enabling deeper imaging through scattering medium by employing spatial illumination.

Typically, four main parameters influence how light propagates inside a scattering medium: the absorption coefficient $\mu_a$ measured in [m−1] that determines the energy loss of the signal; the scattering coefficient $\mu_s$ measured in [m−1] which is a measure of the typical length the light passes between scatterings; the scattering anisotropy g which measures the mean value $<\cos(\theta)>$ where $\theta$ is the scattering deflection angle (it allows calculating how much will the typical scatter be "forward" in direction); and the medium index of refraction n.

From $\mu_z$ and g, the reduced scattering coefficient $\mu_s'$ may be derived, where:

$$\mu_s' = \mu_s * (1-g) \quad (1)$$

which represents the realistic scattering length considering a typical scatter direction. The typical scattering time may be calculated by the reduced scattering coefficient and the index of refraction.

$$t_s' = \frac{\mu_s'}{c_0} n \quad (2)$$

In a realistic imaging case, a pulse of light is projected through the scattering medium towards the sample. As a result of scattering in the medium, the pulse stretches and may be described by ballistic, snake and diffusive signal components. Ballistic components take the shortest path through the medium and preserve image information. In contrast, diffusive light undergoes numerous scatterings, travels long distances inside the scattering medium and does not contribute towards forming a direct image. Snake photons undergo some scatterings in the forward direction, hence retaining some image information. The light then impinges on the sample and is scattered back or transmitted towards a sensor through the scattered medium again.

As before, the signal stretches and can be described by ballistic, snake and diffusive photons.

FIG. 1 is a graph of photon count vs. time for light interacting with scattering medium. Three sections (12, 14 and 16) of photons arriving from an interaction between the illuminated light and the sample through a scattering medium are shown, divided in their time of arrival to the sensor. The first section 12 includes ballistic photons that have reached the sample directly from the illumination source (B1) and ballistic photons that reached the sensor after interacting with the sample (B2). The next section 14, some pico-seconds later, includes two groups of photons: photons that were scattered on their way from the sample to the sensor due to the scattering medium (B1 and P2), and photons that were scattered to the direction of the sample due to the medium, and were ballistic from the sample to the sensor (P1 and B2). The third section 16 includes of photons that were scattered by the sample as well as by the scattering medium, before arriving to the sensor, causing them to arrive last.

Many approaches are known to screen photons that contribute to the image data from photons that do not contribute to the image data. An ideal imaging method should gate the photons of the third section, utilize the photons of the first section and collect the maximal amount of information from the snake photons of the second section.

A short pulse of light less than $t_z'$ is known to have been used, along with time gating of less than 100 ps from the first arrival of light. This requires expensive less-than-several pico-seconds laser source and specialized time gated sensor.

According to some embodiments of the present invention, instead of short pulses and gating in time, a system for imaging through a scattering medium may employ a narrow angle of light collection, thereby omitting scattered photons while maintaining ballistic photons.

Optical systems that include long optical channels absorbing light travelling in angles higher than a predetermined angle (e.g., 0.29°) are known, but may not be suitable for imaging through a scattering medium in real in-vivo conditions. Also, the acquired signal in such systems is typically very weak and prone to be affected by stray light of photons that had been subjected to many scattering, traveling uniformly in all directions.

Employing holography-based approach with short coherence length illumination source may allow for longer pulse times. In this approach, the coherent length may compare with $\mu_z'$, only photons undergoing scattering that results in an optical path of less than the coherence length will contribute to the interference pattern while light that travels longer distances will be averaged and only contribute to a random noise. Increasing the width (the length along the direction of propagation—the ballistic path—of the imaging beam) of the scattering medium may reduce the number of interfering photons, while increasing the averaged noise. Consequently, the signal to noise ratio may reduce blurring and limiting of the reconstruction of the sample's spatial frequencies. Encoding the illumination using modulated phase is known to have been previously done to increase the signal to noise ratio. However, it was assumed that the illumination system is directly illuminating the sample, without being scattered through a scattering medium as in a real in-vivo scenarios. Also, such a method depends on temporal multiplexing which increases the acquisition duration.

According to some embodiments of the present invention, the scattering limitation and high acquisition time may be addressed by using a spatially structured illumination. This may entail autocorrelation of an encoding illumination pattern.

According to some embodiments of the present invention, a system for imaging an object through a scattering medium may include an illumination system, an imaging sensor and a processing unit for processing image data sensed by the imaging sensor.

An illumination system, according to some embodiments of the invention, may include a light source to generate a light beam. In some embodiments, the light source can be, for example, white light source, light emitting diode (LED), a continuous laser source, a pulsed laser source (e.g., femtosecond, picosecond, nanosecond, millisecond pulsed laser source etc.), for generating an imaging light beam.

A spatial encoding pattern generator may be used to encode the imaging beam so as to concurrently illuminate the object by a plurality of different spatial encoding patterns, where each encoding pattern of the different encoding patterns is characterized as having a distinct wavelength of the imaging pattern.

Some of the different encoding patterns may overlap in whole or in part but without being correlated or have a correlation function (between these different encoding patterns) that has sharp maxima at specific points.

An imaging sensor may be used to receive the image beam after it was transmitted through the object or reflected off the object, and a processing unit may be used to reconstruct an image of image data sensed by the sensor.

In the reconstruction of the image of the object, the processing unit may be designed to execute an image reconstruction algorithm that decodes the encoded spatial patterns that illuminated the object and ignores photons that were scattered by the scattering medium, by ignoring any image data representing deviations from the spatial encoding patterns. For example, if a green photon reaches an area that was supposed to be illuminated by other color (or colors), it will be ignored in the reconstruction of the object image, under the assumption that it is not a ballistic photon (e.g., it did not travel directly from the light source to the position it was detected, and was most likely scattered on its way).

In some embodiments of the invention, temporal gating is used, in order to separate ballistic photons from scattered photons. Temporal gating may be achieved, for example, by applying very short laser pulses, by applying short coherence gating (e.g., via interference). Coherence gating may be realized, for example, by taking a first arriving light (FAL) approach, performing coherence shaping of the illumination to obtain a desired temporal gating.

For example, in order to apply FAL approach, a reference beam may be split from the light beam generated by the light source and directed along an alternative optical path into the sensor, allowing interferometry.

Spatial encoding patterns may be obtained, for example by employing Barker based arrays. A set of laterally shifted barker coded patterns (shown on FIG. 1B) may be projected on the sample. The shift may cause pattern scanning of the sample.

A one-dimensional (1D) scanning may enhance a two-dimensional (2D) image in all directions regardless to the original scanning direction Another feature relating to the illumination produced by a system according to some embodiments of the present invention, is that it may project multiple patterns simultaneously in different wavelengths. The shifted-pattern illuminated sample images may then be separated and analyzed (e.g., using wavelength multiplexing) for increased acquisition time.

Figure 1B:
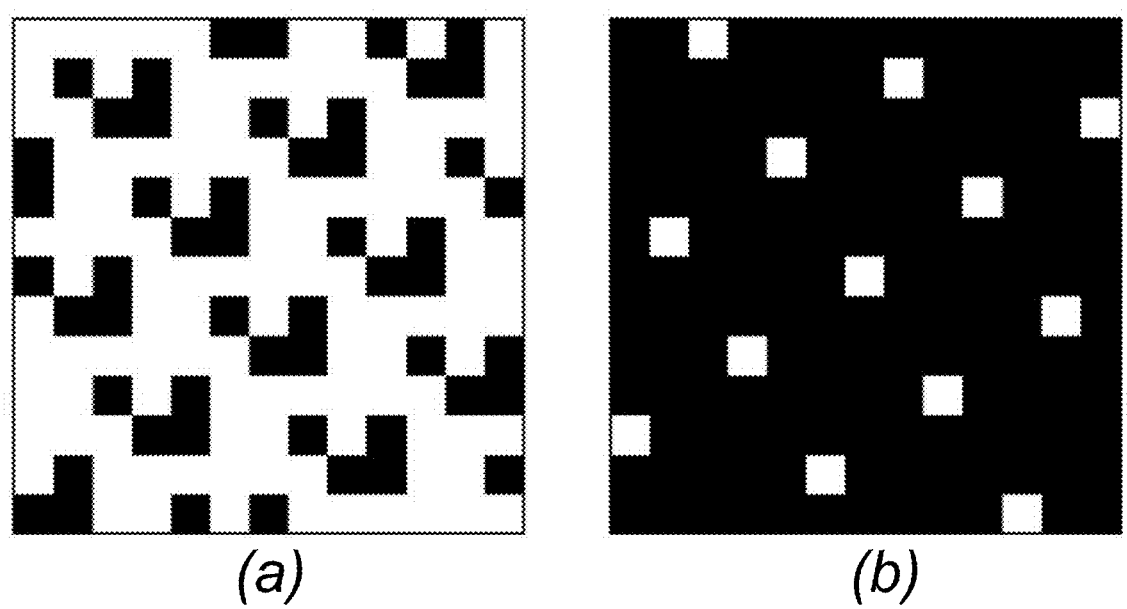
FIG. 1B shows a pair of Barker based arrays, which may be used in a system for imaging through a scattering medium.

FIG. 1B shows a pair of Barker based arrays, which may be used in a system for imaging through a scattering medium. In this example, a 13×13 Barker based array (a), where each row is a 5-pixel shift of a basic Barker encoding vector. Array (b) is an autocorrelation of the Barker array of (a). Other arrangements (other pixel numbers, other encoding vectors) may also be used in some embodiments of the invention.

The coherence length may be calculated in correlation to FIG. 1A. A straightforward approach may involve determining the coherence length such that only photons from the first section will interfere. Increasing the coherence lengths may allow collection of more photons from the middle section adding both to the signal and noise. The spatial encoding then eliminates noise coming from B1+P2 photons that do not contribute to the data, while preserving the snake photons that do contribute.

Figures 2A, 2B:
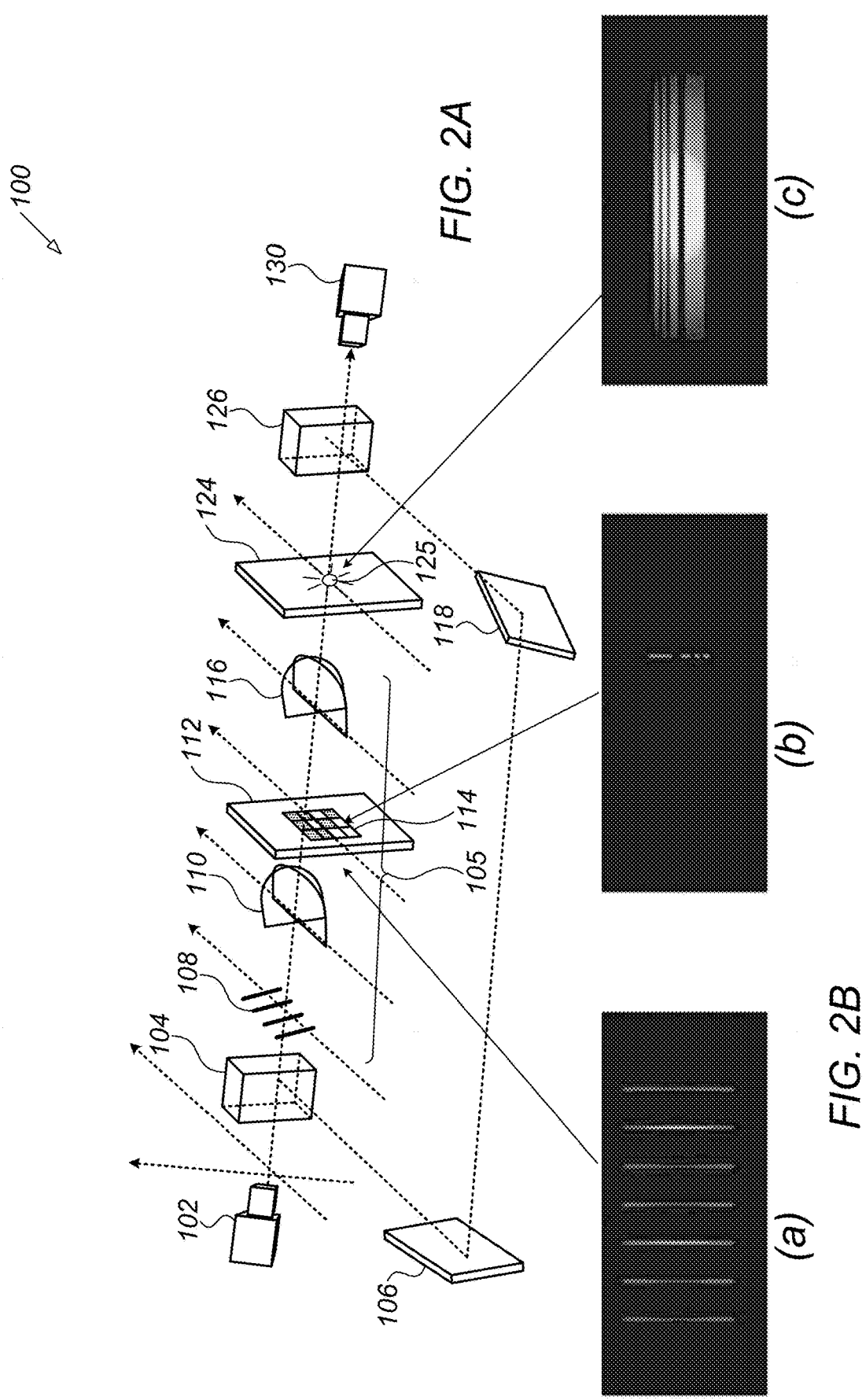
FIG. 2A illustrates a system for imaging through a scattering medium, according to some embodiments of the present invention, using one-dimensional illumination pattern.
FIG. 2B shows images of the light intensity of a specific wavelength on different planes, according to some embodiments of the invention.

FIG. 2A illustrates a system for imaging through a scattering medium, according to some embodiments of the present invention, using one-dimensional illumination pattern. This system may be designed to perform different spatially encoding for different wavelengths of an illumination beam to perform resolution enhancement and to see beyond a scattering tissue.

System 100 includes an illumination source 102, e.g., a laser beam generator, such as a continuous laser, pulsed laser (e.g., femtosecond, picosecond pulsed laser in some embodiments, and nanosecond or a millisecond pulsed laser in other embodiments—faster pulses may better contribute to high-resolution imaging results). A light beam generated by the light source 102 may be split by a beam splitter 104 into two beams. One beam serves as a reference beam and is directed by mirrors (106 and 118) through a second beam splitter 126 into optical imaging sensor 130. The other beam, referred hereinafter as the imaging beam, is directed through a spatial encoding pattern generator 105, for example a series of optical elements. According to some embodiments of the invention, the spatial encoding pattern generator is configured to image a plurality of different spatial encoding patterns onto an object to be imaged across a first axis that is perpendicular to a direction of propagation the imaging beam and configured to perform a Fourier transform of said plurality of different spatial encoding patterns onto the object across a second axis that is both perpendicular to the first axis and to the direction of propagation of the imaging beam.

First, the imaging beam traverses through a diffraction grating grid G1 108, e.g., 300 lines per mm, other gratings may be in the range of 200 to 2/lambda (the central illumination wavelength) grating lines per mm and is diffracted into a plurality of parallel beams which are then Fourier-transformed in the X-axis direction, when passing through cylindrical lens L1. L1 is characterized as having two different foci length values for each of the two orthogonal axes (e.g., f in the Y-axis and 2f in the X-axis, such as, for example, 25.4 mm and 50.8 mm, respectively) Diffraction grating grid G1 108 is distanced from L1 by 2f (the X-axis focal length of L1) so that the Fourier conjugated plane in the X axis is located at the X-axis focal point of L1, and the imaging plane of the beam is located at the Y-axis focal point. This causes the imaging beam to separate into multiple beams of different wavelengths at different deflected locations, corresponding to their wavelength in the X-plane, with the beam original height in the Y-plane maintained. Encoding pattern element 112 (e.g., two Barker based arrays 114, such as, for example, the ones depicted in FIG. 1B) is further provided down the propagation direction of the imaging beam, located at a distance of 2f (the X-axis focal length of L1) from L1, to encode each beam of the multiple beams of different wavelengths accordingly. Next, the imaging beam traverses through lens L2 116 which again has an X-axis focal length of twice the focal length of that lens in the Y-axis (e.g., 25.4 mm and 50.8 mm, respectively). Encoding pattern element 112 is distanced by 2f from L1 110 (the X-axis focal length of L1), at which point an image of the encoding pattern in the Y axis is formed, and lens L2 116, located at a distance of 2f (the X-axis focal length of L1) and serves for widening the imaging beam in the X axis back to its original width.

Light emerging from L2 116 is directed onto a sample (e.g., tissue within a body of a patient), which may be located at a distance of 2f from L2 (the X-axis focal length of L2). Light transmitted through the sample and is collected by optical imaging sensor 130. A beam splitter 126 may be placed in the way, for combining the reference beam with the imaging beam before impinging the optical imaging sensor 130.

The corresponding X-axis focal lengths Y-axis focal lengths of L1 and L2 may be same or different.

FIG. 2B shows images of the light intensity of a specific wavelength on different planes, according to some embodiments of the invention. Image (a) shows the intensity image of the imaging beam as it reaches L1, at the X-axis focal plane, just before the encoding pattern. Image (b) shows the intensity image of the imaging beam after traversing the encoding pattern. Only one line has evidently passed, encoded in the Y-axis. Image (c) is the projected intensity of the imaging beam on the object.

Eventually, the result for each wavelength (of the multiple wavelengths emerging from L1), in the example of FIG. 2, is a spot which follows the encoded pattern in the Y axis and the original beam profile in the X axis. Each wavelength will produce a different pattern on the object, according to the encoding pattern.

Using the encoding pattern to introduce a set of laterally shifted patterns (for example a 2D image, encoded a pattern of a single row in the pattern shown on FIG. 2, shifting the encoding row for each wavelength), we can uphold the image enhancement and coherence gated signal as explained in the introduction.

Figure 3:
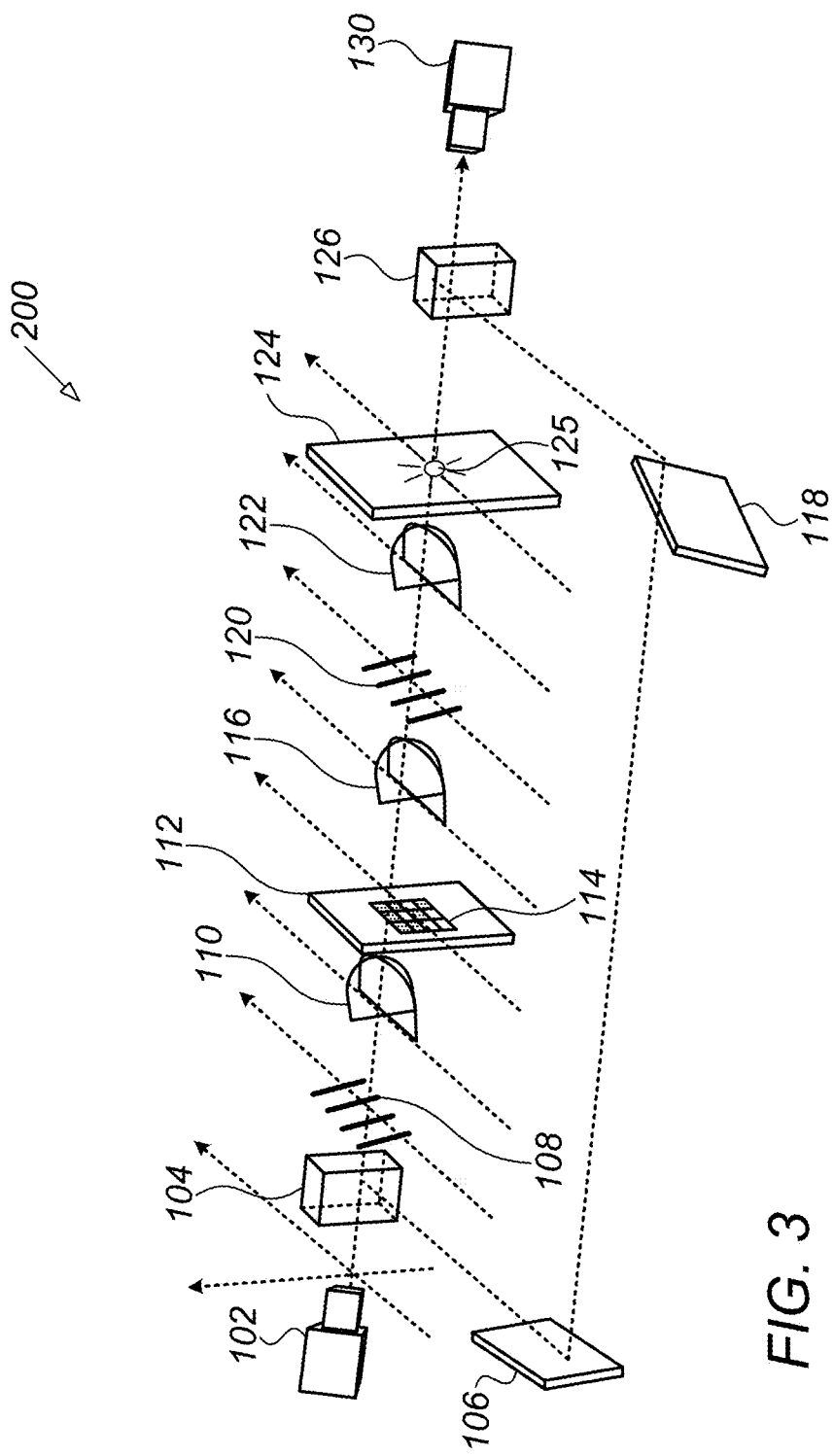
FIG. 3 illustrates a system for imaging through a scattering medium, according to some embodiments of the present invention, using two-dimensional illumination pattern.

FIG. 3 illustrates a system for imaging through a scattering medium, according to some embodiments of the present invention, using two-dimensional illumination pattern.

System 200 is designed similarly to system 100 of FIG. 2A but has some additional optical elements in the spatial encoding pattern generator, in the following order along the optical path of the spatial encoding pattern generator: a second diffraction grating grid 120, and a third lens L3 122. The third lens L3 122 has an X-axis focal length of twice the focal length of that lens in the Y-axis (e.g., 25.4 mm and 50.8 mm, respectively).

The diffraction grating grid 120 (e.g., 300 lines per mm, other gratings may be in the range of 200- to 2/lambda (the central illumination wavelength) grating lines per mm) is positioned at the X-axis focal point of lens 116 and at the X-axis focal point of lens L3 122.

The focal lengths (X, Y) of the lenses are not necessarily the same (in either of the systems depicted in FIG. 2B and FIG. 3).

The spatial encoding pattern projection generated in this setup is two-dimensional as a result of the added optical elements.

Some embodiments of the present invention may utilize discrete wavelength encoded patterns. Some embodiments of the present invention may utilize continuous wavelength (bands) encoded patterns.

The second diffraction grating Grid G2 120 may be designed to fulfil the required functionality.

For example, for discrete wavelengths G2 is designed to have a frequency of $$\frac{f_{L1x}}{f_{L2x}} v_0$$

where $v_0$ is the frequency of G1, $f_{L1x}$ and $f_{L2x}$ are the X-axis focal lengths of L1 and L2.

For continuous wavelength bands, a grid with single frequency G2 may have a frequency $\Delta\Omega$ such that:

$$\Delta\Omega = \frac{\frac{f_{L1x}}{f_{L2x}} v_0 \Delta\lambda}{N_{num}(\lambda_0 + \Delta\lambda)},$$

where $N_{num}$ is the number of different patterns that will be projected on the object, $\lambda_0$ is the minimal projection wavelength and $\Delta\lambda$.

Using the encoding pattern to introduce a set of laterally shifted patterns (for example, a 2D image of the pattern shown on FIG. 1B, circle shifting the encoding by a pixel in the horizontal direction for each wavelength), the image reconstruction may be enhanced, and coherence gated signal obtained as explained hereinabove.

Mathematical description of the optical setup of the spatial encoding pattern generator is provided below:

For plane $U(X_0, Y_0)$, assuming a constant wave front, and a tilt toward the grid $\theta$:

$$u_0(x_0, y_0) = \exp\left(i\frac{2\pi}{\lambda} x_0 \cdot \sin\theta\right) \tag{3}$$

Plane $U(X_1, Y_1)$ behind grid G1 with frequency $v_0$:

$$u_1(x_1, y_1) = \exp\left(i\frac{2\pi}{\lambda} x_1 \cdot \sin\theta\right) \sum_n \delta(x_1 - v_0 \cdot n) \tag{4}$$

Plane $U(X_2, Y_2)$ Fourier transform with scaling by f1*lambda we assume we take only the first diffraction order and get:

$$u_2(x_2, y_2) = \delta\left(x_2 - \left[v_0 + \frac{\sin\theta}{\lambda}\right]\lambda f_1\right) \tag{5}$$

$$u_2(x_2, y_2) = \delta(x_2 - [f_1 \cdot \sin\theta + f_1 v_0 \lambda])$$

For discrete wavelengths:

The lenses have different foci such that the length between $U(x1,y1)$ to plane $U(x2,y2)$ is fx=2*fy, so imaging in the y plane and Fourier transform in the x plane may be created.

In the X plane, the lens has a limited diameter aperture D such that in plane $U(x2,y2)$ there is enough place to place a pattern, with minimal change in illumination intensity:

$$u_2(x_2, y_2) = \delta\left(x_2 - \left[v_0 + \frac{\sin\theta}{\lambda}\right]\lambda f_1\right)\text{sinc}(D \cdot x_2) \tag{6}$$

$$u_2(x_2, y_2) = \delta(x_2 - [f_1 \cdot \sin\theta + f_1 v_0 \lambda])\text{sinc}(D \cdot x_2)$$

The spatial encoding pattern element (encoding mask) may be placed before the focal plane of L1 so as to get again a sinc function of the same diameter.

Figure 4:
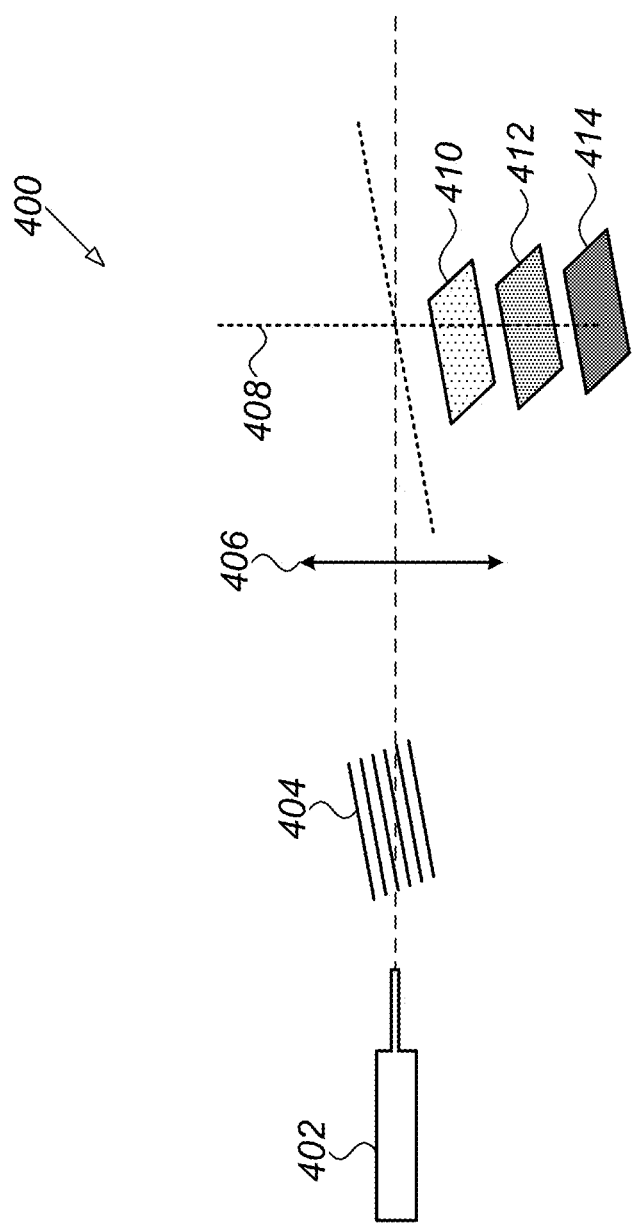
FIG. 4 illustrates discrete light illumination achieved by a system for imaging through a scattering medium, according to some embodiments of the present invention.

In these conditions, before the encoding mask, different color spots in discrete locations may be obtained, centered in $[f_1 \cdot \sin\theta + f_1 v_6 \lambda]$. For each location, an encoding pattern may be matched, as illustrated in FIG. 4. The laser source 402 in system 400 generates an imaging beam that traverses grating grid 404, lens 406 and illuminates discrete separated spots of color—blue 410, green 412 and red 414 onto spatial encoding pattern element 408.

Plane $X_3$ multiply with coding pattern:

$$u_3(x_3, y_3) = \text{Sinc}\left(\frac{x_3[f_1 \cdot \sin\theta + f_1 v_0 \lambda]}{D}\right) B(x_3 - f_1 v_0 \lambda_{min}) \qquad (7)$$

Plane $X_4$ Fourier transform with scaling by f2*lambda:

$$U_3 = F(u_3(x_3, y_3)) = u_4(x_4, y_4) = U_3\left(\frac{x_4}{\lambda f_2}, \frac{y_4}{\lambda f_2}\right) \qquad (8)$$

Introducing grid2:
To unite the spots together grid2 should be the same as $$G2 = \frac{f_1}{f_2} v_0 \cdot u_5(x_5, y_5) = u_4(x_4, y_4) \sum_n \delta(x_1 - v_0 \cdot n) = \qquad (9)$$

$$U_3\left(\frac{x_5}{\lambda f_2}, \frac{y_5}{\lambda f_2}\right) \sum_n \delta\left(x_5 - \frac{f_1}{f_2} v_0 \cdot n\right)$$

Plane $X_6$ Fourier transform:

$$u_6(x_6, y_6) = \cdot \left(\text{Sinc}\left(\frac{x_6[f_1 \cdot \sin\theta + f_1/f_2 v_0 \lambda]}{D}\right) \right. \qquad (10)$$

$$\left. B(x_3 - f_1 * v_0 \lambda) \otimes \sum_{m=0}^{-\infty} \delta\left(x - \lambda\left(\frac{f_1}{f_2} v_0 \cdot n\right)\right)\right)$$

which means that the grid deflects each wavelength to the optical axis position regardless of the wavelength.

Another solution involves generating continuous wavelength bands, one frequency grating.

The lenses have different foci such that the length between U(x1,y1) to plane U(x2,y2) is fx=2*fy so imaging in the y plane and Fourier transform in the x plane may be obtained.

In the X plane, aperture D may be opened such that, in plane U(x2,y2), a delta function exists for each wavelength:

Plane $X_3$ multiply with coding pattern:

$$u_3(x_3, y_3) = \delta(x_3 - [f_1 \cdot \sin\theta + f_1 v_0 \lambda]) B(x_3 - f_1 v_0 \lambda_{min}) \qquad (11)$$

Note that, in the discussed example, the encoding pattern is built from $N_p$ discrete pixels of size $\Delta X_{pt}$, which means that each pattern may require length of $L_{pt} = N_p \Delta X_{pt}$, if $N_{num}$ different patterns are desired, a spot of size $L_{num} = N_{num} L_{pt} = N_{num} N_p \Delta X_{pt}$ may be needed.

This means that the laser spectral band should be:

$$f_1 v_0 \Delta \lambda = N_{num} N_p \Delta X_{pt} \quad \Delta \lambda = \frac{N_{num} N_p \Delta X_{pt}}{f_1 v_0} \qquad (12)$$

Plane $X_4$ Fourier transform with scaling by f2*lambda:

$$u_4(x_4, y_4) = B([f_1 \cdot \sin\theta + f_1 v_0 (\lambda - \lambda_{min})]) \qquad (13)$$

$$\exp\left(-i \cdot 2\pi \frac{(f_1 \cdot \sin\theta + f_1 v_0 \lambda)}{\lambda f_s} x_4\right) = u_4(x_4, y_4) =$$

$$B([f_1 \cdot \sin\theta + f_1 v_0 (\lambda - \lambda_{min})]) \exp\left(-i \cdot 2\pi \frac{f_1}{f_2}\left(\frac{\sin\theta}{\lambda} + v_0\right) x_4\right)$$

Introducing grid G2 with only one frequency:
Assuming that $f_1 = f_2$ and $\theta = 0$:

$$G_{2b} = \sum_{m=\infty}^{-\infty} \delta\left(x - \frac{1}{\Delta\Omega \cdot n} m\right) \text{rect}\left(\frac{x - nW_z}{W_z}\right) \qquad (14)$$

Where $\Delta\Omega$ will currently be undetermined
Plane $X_5$ multiply with grid2:

$$u_5(x_5, y_5) = \qquad (15)$$

$$B([f_1 \cdot \sin\theta + f_1 v_0 (\lambda - \lambda_{min})]) \exp\left(-i \cdot 2\pi \frac{(f_1 \cdot \sin\theta + f_1 v_0 \lambda)}{\lambda f_s} x_5\right) \cdot$$

$$\sum_{m=\infty}^{-\infty} \delta\left(x - \frac{1}{\Delta\Omega \cdot n} m\right) \text{rect}\left(\frac{x - nW_z}{W_z}\right)$$

Plane $X_6$ Fourier transform:

$$u_6(x_6, y_6) = \cdot \qquad (16)$$

$$\left(B(f_1 \cdot \sin\theta + f_1 v_0 (\lambda - \lambda_{min})) \left[\delta\left(x_6 - \lambda f_3 v_0 - \frac{f_1}{f_2} f_3 \cdot \sin\theta\right)\right] \otimes \right.$$

$$\sum_{m=\infty}^{-\infty} \delta(x - \lambda f_3 (\Delta\Omega \cdot n)) \otimes$$

$$\left. \left(\text{sinc}\left(\frac{x}{\frac{\lambda f_3}{W_z}}\right) \exp\left(-i \cdot 2\pi\left(\frac{nW_z}{\lambda f_2}\right) x_5\right)\right)\right)$$

Figure 5:
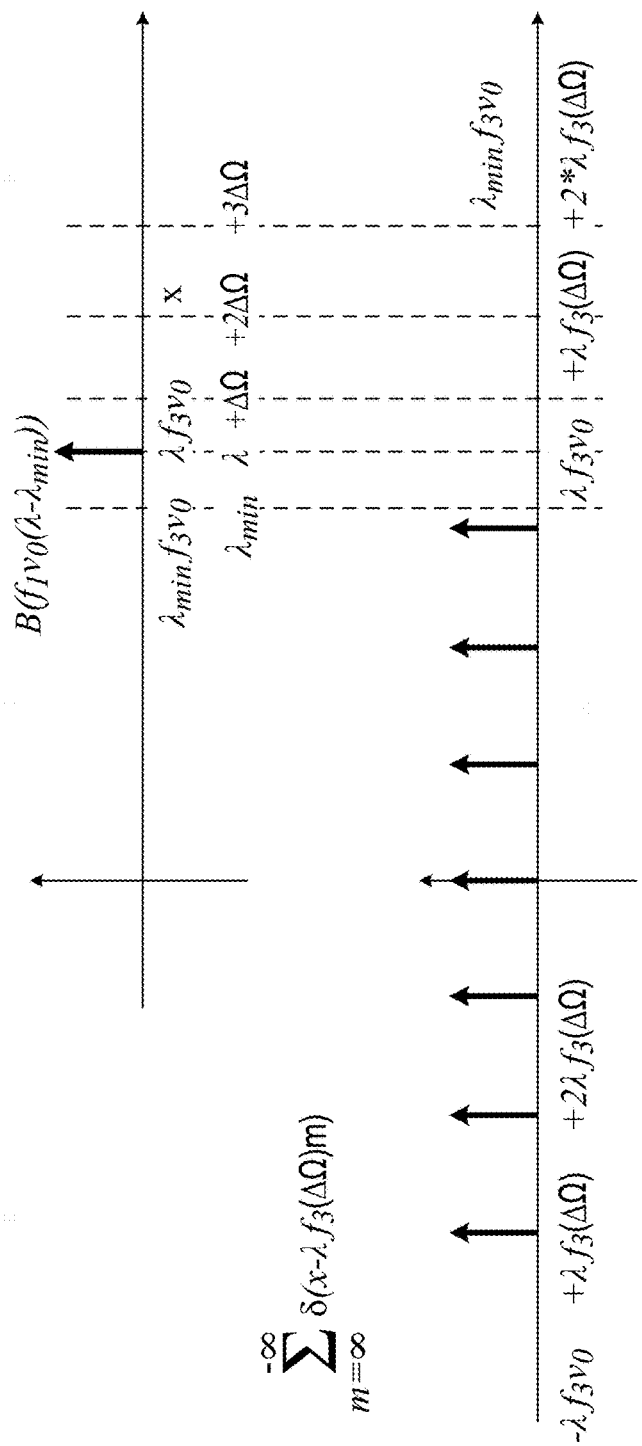
FIG. 5 illustrates convolutional components for a single wavelength, in light illumination achieved by a system for imaging through a scattering medium, according to some embodiments of the present invention.

For a single wavelength, FIG. 5 demonstrates Eq. 10 convolutional components for a single wavelength. On top is the equation's left component, at the bottom is the equation's right component, and the final convolution per wavelength is depicted in FIG. 6.

Figure 6:
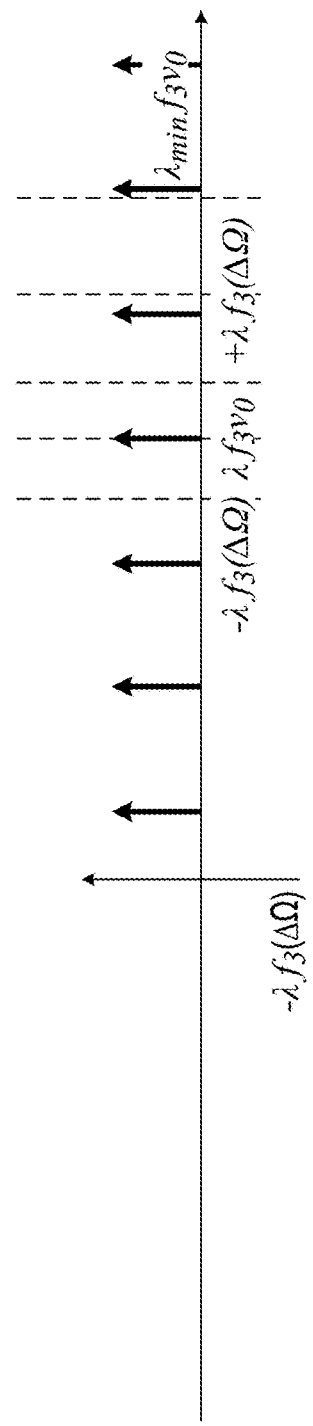
FIG. 6 illustrates final convolutional for a single wavelength, in light illumination achieved by a system for imaging through a scattering medium, according to some embodiments of the present invention.

FIG. 6 shows Eq. 10 relating to the final convolution for a single wavelength.

So, with an infinite amount of orders, the entire space may be covered with encoding patterns, but a scaled barker code may be required.

The minimal wavelength location is:

$$x_0 = \lambda_0 f_3 v_0 \qquad (11)$$

The next wavelength that overlaps with the first is:

$$\lambda_0 f_3 v_0 = \lambda_1 f_3 (v_0 - \Delta\Omega)$$

In general, the n-th overlap is:

$$\lambda_n = \lambda_0 \frac{(v_0)}{(v_0 - n \cdot \Delta\Omega)} \qquad (17)$$

To use the whole bandwidth, the grid frequency is taken such that exactly $N_{num}$ replicas are obtained:

$$\lambda_n - \lambda_0 = \Delta\lambda = \lambda_0 \left( \frac{(v_0)}{(v_0 - (N_{num})\Delta\Omega)} - 1 \right) = \lambda_0 \left( \frac{(N_{num}) \cdot \Delta\Omega}{(v_0 - (N_{num})\Delta\Omega)} \right) \quad (18)$$

And finally:

$$\Delta\Omega = \frac{v_0 \Delta\lambda}{N(\lambda_0 + \Delta\lambda)} \quad (19)$$

If $f_1 \neq f_2$ and $\theta=0$: $v_0$ is everywhere, then it is replaced by $$\frac{f_1}{f_2} v_0 :$$

$$\lambda_0 f_2 \left( \frac{f_1}{f_2} v_0 \right) = \lambda_1 f_3 \left( \frac{f_1}{f_2} v_0 - \Delta\Omega \right)$$

In general, the n-th overlap is:

$$\lambda_n = \lambda_0 \frac{\left( \frac{f_1}{f_2} v_0 \right)}{\left( \frac{f_1}{f_2} v_0 - n \cdot \Delta\Omega \right)} \quad (20)$$

$$\lambda_n - \lambda_0 =$$

$$\Delta\lambda = \lambda_0 \left( \frac{\frac{f_1}{f_2} v_0}{\frac{f_1}{f_2} v_0 - (N_{num}) \cdot \Delta\Omega} - 1 \right) = \lambda_0 \left( \frac{(N_{num}) \cdot \Delta\Omega}{\left( \frac{f_1}{f_2} v_0 - (N_{num}) \cdot \Delta\Omega \right)} \right)$$

$$\Delta\Omega = \frac{\frac{f_1}{f_2} v_0 \Delta\lambda}{N_{num}(\lambda_0 + \Delta\lambda)} \quad (21)$$

Note that, from Eq. (14), that each pattern regime $\lambda_n - \lambda_{n-1}$ has different spectral size so the pattern should be scaled in each pattern region.

Figure 7:
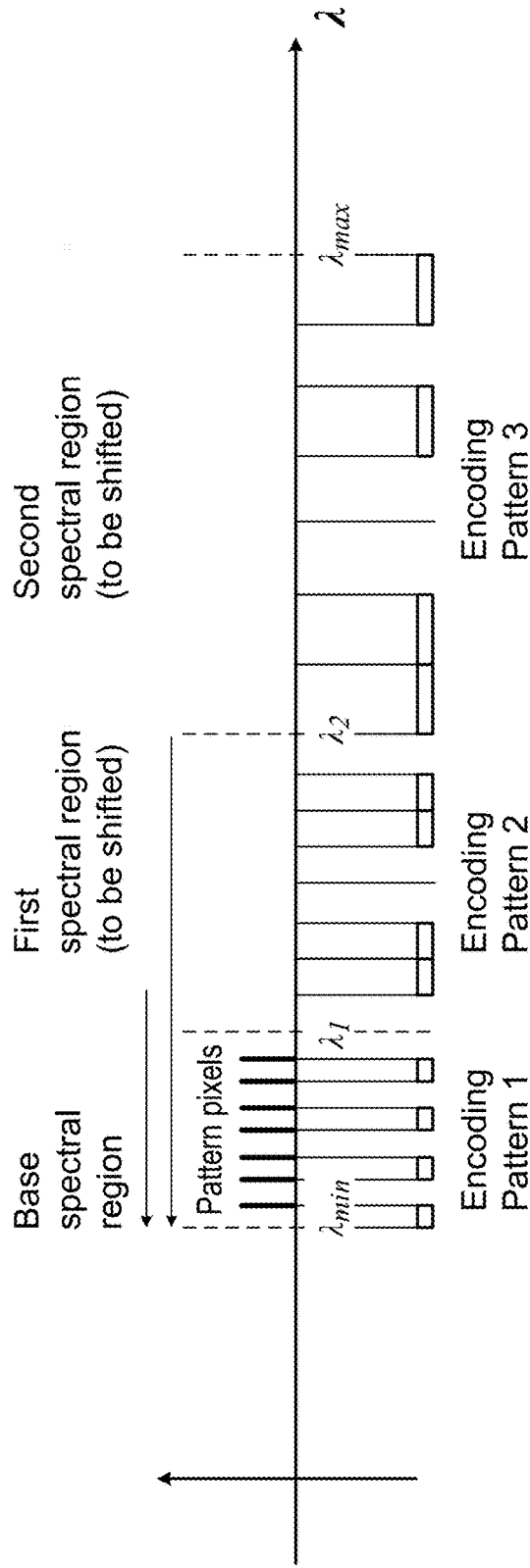
FIG. 7 illustrates spectral regions and pattern pixels for continuous wavelength encoding using a single frequency grating, according to some embodiments of the present invention.

FIG. 7 shows an illustration of the spectral axis where the different spectral regions are marked. The wavelengths that start each region are marked in black dashed line. Each region would eventually be shifted to the Base spectral region.

The pattern pixel in each region are scaled to fit n equally spaced pixels in the base spectral region. At the bottom of the figure each pattern pixel is illustrated by the dual line and the different patterns are illustrated by filling the space inside the designated pattern pixel. The encoding pattern put in the L1 lens X-axis focal should consist of the whole encoding patterns in these wavelengths corresponding location, as illustrated by the total pattern on the bottom.

Figure 8:
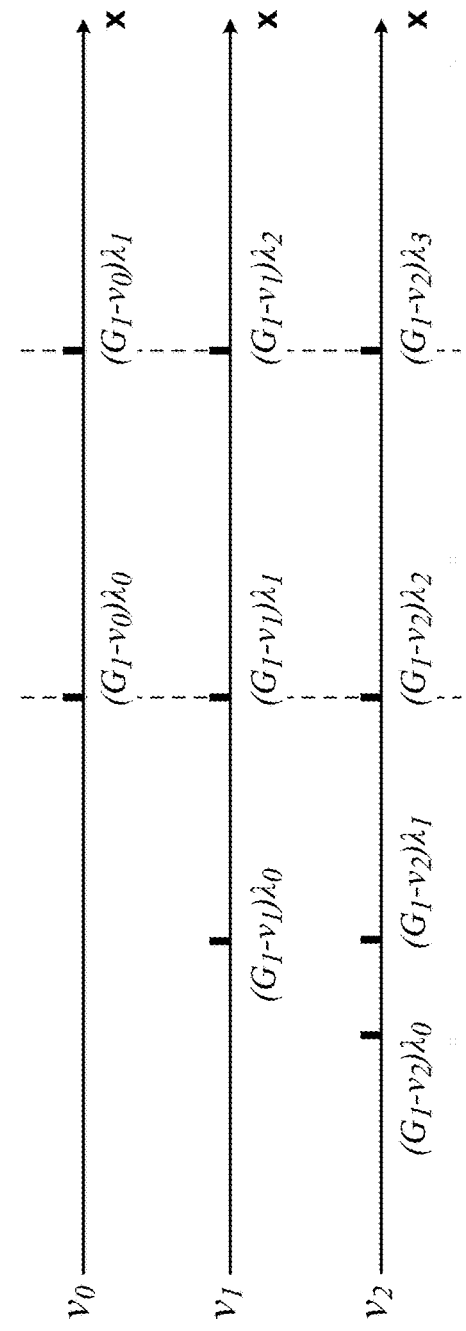
FIG. 8 illustrates Deflection of each second grating grid frequency on the spatial axis plane, according to some embodiments of the present invention.

FIG. 8 illustrates spectral regions and pattern pixels of solution 2. The n-th spectral regime has an area of $\lambda_n - \lambda_{n-1}$ having different spectral size to each region. The pixels in the regimes are marked by dotted lines, each pattern fills different spectral pixels differently. Eventually the encoding mask includes the same patterns as illustrated here, in the corresponding locations in the spatial axis of the plane in the X-axis focal plane of lens L1.

To find the scale, Np pixels are equally spaced in the first regime, From Eq. (14) and Eq. (15), the first pattern overlap by the grid multiplication is:

$$\lambda_1 =$$

$$\lambda_0 \frac{\left( \frac{f_1}{f_2} v_0 \right)}{\left( \frac{f_1}{f_2} v_0 - 1 \cdot \Delta\Omega \right)} = \lambda_0 \frac{\left( \frac{f_1}{f_2} v_0 \right)}{\left( \frac{f_1}{f_2} v_0 - \frac{\frac{f_1}{f_2} v_0 \Delta\lambda}{N_{num}(\lambda_0 + \Delta\lambda)} \right)} = \frac{\lambda_0}{\left( 1 - \frac{\Delta\lambda}{N_{num}(\lambda_0 + \Delta\lambda)} \right)}$$

And the first regime is $\lambda_1 - \lambda_0$ Divided to Np Equally spaced pixels, each pixel length is:

$$\left( \frac{\lambda_1 - \lambda_0}{N_p} \right) = m \cdot \left( \frac{\lambda_0}{N_p} \left( \frac{1}{\left( 1 - \frac{\Delta\lambda}{N_{num}(\lambda_0 + \Delta\lambda)} \right)} - 1 \right) \right) =$$

$$m \cdot \frac{\lambda_0}{N_p} \left( \frac{\frac{\Delta\lambda}{N_{num}(\lambda_0 + \Delta\lambda)}}{\left( 1 - \frac{\Delta\lambda}{N_{num}(\lambda_0 + \Delta\lambda)} \right)} \right) = m \cdot \frac{\lambda_0}{N_p} \left( \frac{1}{\left( \frac{N_{num}(\lambda_0 + \Delta\lambda)}{\Delta\lambda} - 1 \right)} \right)$$

And the starting spectral wavelength of each pixel is:

$$\lambda_{0,m} = \lambda_0 + m \cdot \left( \frac{\lambda_1 - \lambda_0}{N_p} \right) = \lambda_0 \left( 1 + \frac{m}{N_p} \cdot \frac{1}{\left( \frac{N_{num}(\lambda_0 + \Delta\lambda)}{\Delta\lambda} - 1 \right)} \right) \quad (22)$$

So, in each n-th replica, the starting spectral wavelength of the m-th pixel is:

$$\lambda_{n,m} = \frac{\lambda_{0,m} \cdot \frac{f_1}{f_2} v_0}{\frac{f_1}{f_2} v_0 - n \cdot \Delta\Omega} = \lambda_0 \frac{\left( 1 + \frac{m}{N_p} \cdot \frac{1}{\left( \frac{N_{num}(\lambda_0 + \Delta\lambda)}{\Delta\lambda} - 1 \right)} \right)}{1 - n \frac{\Delta\Omega}{\frac{f_1}{f_2} v_0}} = \quad (23)$$

$$\lambda_0 \frac{\left( 1 + \frac{m}{N_p} \cdot \frac{1}{\left( \frac{N_{num}(\lambda_0 + \Delta\lambda)}{\Delta\lambda} - 1 \right)} \right)}{1 - \frac{n}{N_{num}} \cdot \frac{\Delta\lambda}{(\lambda_0 + \Delta\lambda)}}$$

Solution 3: suggestion for continuous wavelengths, multiple-frequency grating.

In the previous section, it was shown that grid G2 which includes one frequency that folds the projection illumination in G1 deflection location of the minimal wavelength.

Instead, this can be done using a different G2 grating with multiple frequencies, each of which will deflect a different wavelength towards the desired location. An advantage of this method is that it deflects the imaging beam closer to the optical axis then the single-frequency grid method.

To calculate the needed frequencies and the wavelengths that will start each new pattern, an iterative connection may be considered as follows:

$$\lambda_1, v_1$$
$$\lambda_2 = \lambda_1 + \frac{\Delta L}{((G_1 - v_1)f_3)}, v_2 = G_1 - (G_1 - v_0)\frac{\lambda_1}{\lambda_2} \quad (24)$$
$$\lambda_n = \lambda_{n-1}\frac{G_1 - v_{n-2}}{G - v_{n-1}}, v_n = v_{n-1} + \frac{\Delta L}{f_3 \cdot \lambda_n}$$

In this case, the replicas in the optical axis could be illustrated in FIG. 8. Deflection of each new G2 grid frequency on the spatial axis plane is demonstrated in this figure. Three example grid frequencies are shown. The thicker lines (over the lambda (λ) axis) mark the separating wavelengths between each different encoding pattern frequency.

Applying the iteration relationship above forces each new frequency in the grid to deflect the wavelengths to a known location such that sections in the laser source bandwidth remain in between the specific calculated wavelengths in the specific section. Note that, while in the first spatial section between $(G1-v_0)\lambda_0$ to $(G1-v_0)\lambda_1$ the set of spatial encoding patterns is complete, the spatial region may be enlarged by taking additional wavelengths, shifting, or projecting to another time in the wavelengths that do reach the spatial locations.

In the reconstruction of the image of the object, the image of each encoding pattern of the different encoding patterns that is retrieved from the encoded imaging beam reflected from or transmitted through the object may be multiplied by a corresponding decoding pattern to obtain a product and all of the products may be summed up to obtain the reconstructed image of the object.

According to some embodiments of the present invention, decoding in the abovementioned way is suitable for imaging through a scattering medium as well as for increasing imaging resolution to super-resolution.

Figure 9:
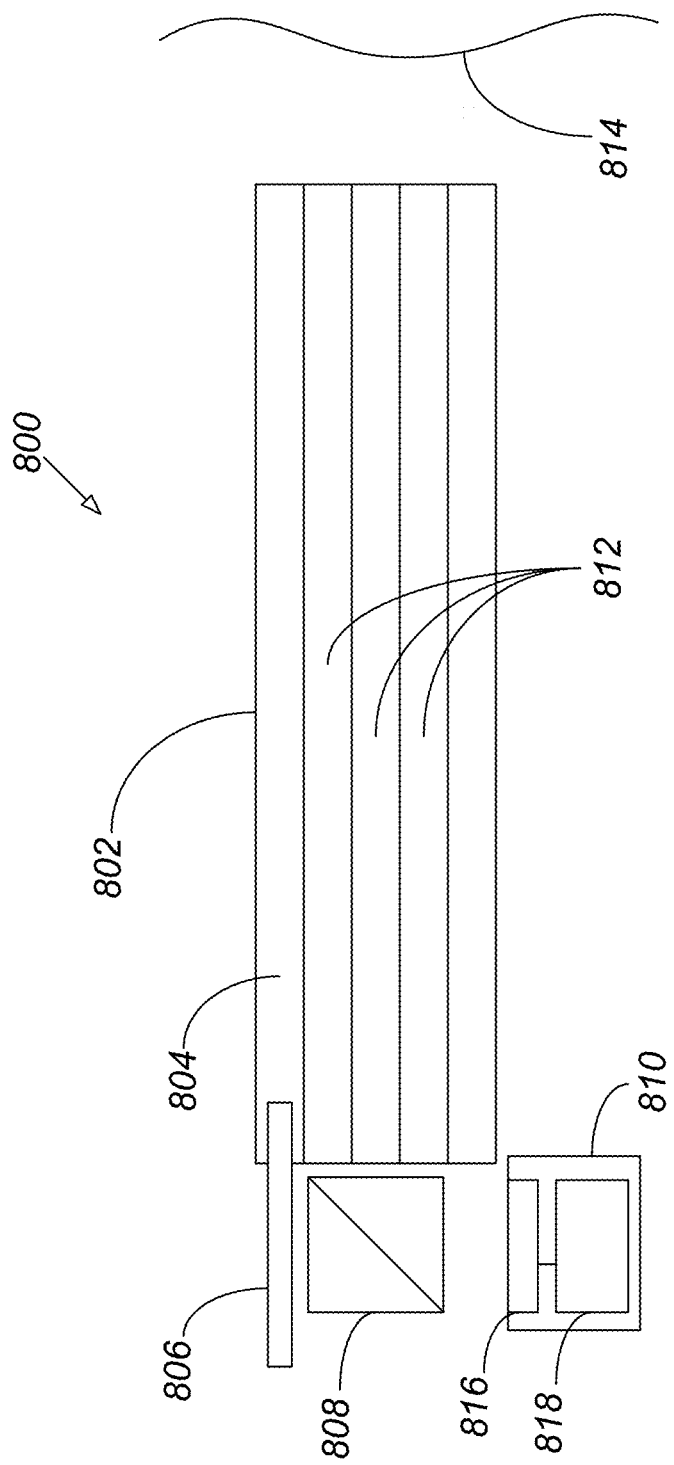
FIG. 9 illustrates a multicore fiber endoscope incorporating a system for imaging an object through scattering medium, according to some embodiments of the present invention.

FIG. 9 illustrates a multicore fiber endoscope 800 incorporating a system for imaging an object through scattering medium, according to some embodiments of the present invention. Endoscope 800 may include an elongated multicore fiber body 802 with one or a plurality of illumination fibers 804, and one or a plurality of imaging fibers 812. A spatial encoding pattern generator 806 may be provided, optically linked to illumination fiber or fibers 804, that are designed to guide plurality of different spatial encoding patterns generated by the spatial encoding pattern generator 806 through the endoscope body 802 out of its distal end so as to illuminate an object 814 (e.g., a tissue inside a patient's body). The imaging fiber or fibers 812 of the endoscope receive the reflected illumination light from the object 814 and transmit it (e.g., via beam splitter 808 into imaging device 810, that includes an imaging sensor 816 and a processing unit 818.

Figure 10:
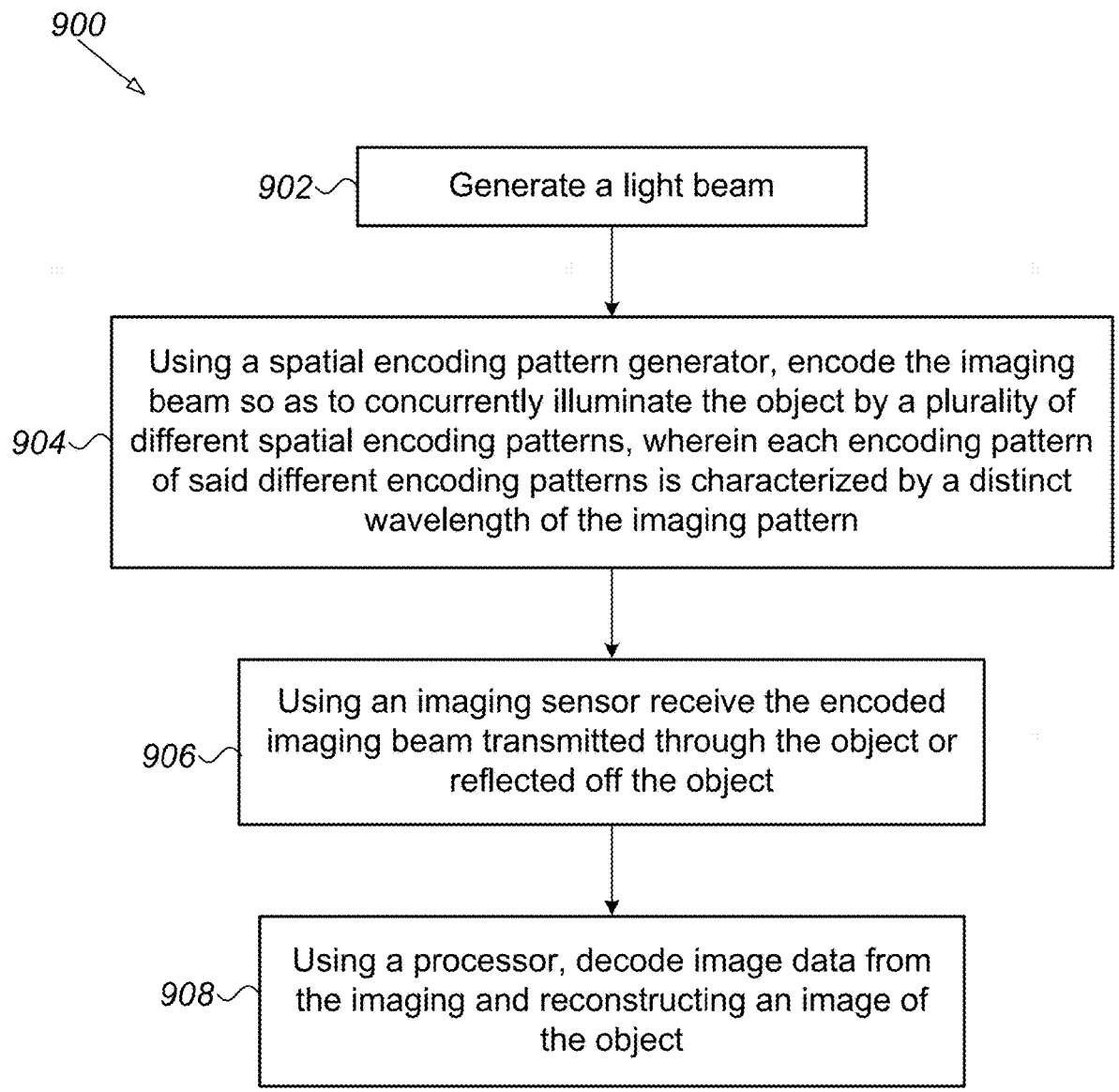
FIG. 10 is a diagram of a method for imaging an object through a scattering medium, according to some embodiments of the present invention.

FIG. 10 is a diagram of a method for imaging an object through a scattering medium, according to some embodiments of the present invention. Method 900 may include generating 902 a light beam. Method 900 may also include using a spatial encoding pattern generator, encoding 904 the imaging beam so as to concurrently illuminate the object by a plurality of different spatial encoding patterns, wherein each encoding pattern of said different encoding patterns is characterized by a distinct wavelength of the imaging pattern.

Method 900 may also include using an imaging sensor, receiving 906 the encoded imaging beam transmitted through the object or reflected off the object, and using a processor, decoding 908 image data from the imaging and reconstructing an image of the object.

Some embodiments of the present invention may be embodied in the form of a system, a method or a computer program product. Similarly, some embodiments may be embodied as hardware, software or a combination of both. Some embodiments may be embodied as a computer program product saved on one or more non-transitory computer readable medium (or media) in the form of computer readable program code embodied thereon. Such non-transitory computer readable medium may include instructions that when executed cause a processor to execute method steps in accordance with examples. In some examples, the instructions stored on the computer readable medium may be in the form of an installed application and in the form of an installation package.

Such instructions may be, for example, loaded by one or more processors and get executed.

For example, the computer readable medium may be a non-transitory computer readable storage medium. A non-transitory computer readable storage medium may be, for example, an electronic, optical, magnetic, electromagnetic, infrared, or semiconductor system, apparatus, or device, or any combination thereof.

Computer program code may be written in any suitable programming language. The program code may execute on a single computer system, or on a plurality of computer systems.

Some embodiments are described hereinabove with reference to flowcharts and/or block diagrams depicting methods, systems and computer program products according to various embodiments.

Features of various embodiments discussed herein may be used with other embodiments discussed herein. The foregoing description of the embodiments has been presented for the purposes of illustration and description. It is not intended to be exhaustive or limiting to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes that fall within the true spirit of the present invention.

The invention claimed is:

1. An illumination system comprising:
 a light source to generate a light beam; and
 a spatial encoding pattern generator comprising one or a plurality of optical elements to encode the light beam forming an imaging beam so as to concurrently illuminate an object by a plurality of different spatial encoding patterns, wherein each encoding pattern of said different encoding patterns is characterized by a distinct wavelength of the imaging pattern,
 wherein said one or a plurality of optical elements to encode the imaging beam are aligned along an optical path in the following order: a diffraction grating grid, a first lens, an encoding pattern element, and a second lens, and
 wherein the first lens is distanced from the diffraction grating grid and from the encoding pattern element by a distance equal to an X-axis focal length of the first lens, and wherein the second lens is distanced from the encoding pattern element by a distance equal to an X-axis focal length of the second lens.

2. An illumination system comprising:
a light source to generate a light beam; and
a spatial encoding pattern generator comprising one or a plurality of optical elements to encode the light beam forming an imaging beam so as to concurrently illuminate an object by a plurality of different spatial encoding patterns, wherein each encoding pattern of said different encoding patterns is characterized by a distinct wavelength of the imaging pattern,
wherein said one or a plurality of optical elements to encode the imaging beam are aligned along an optical path in the following order: a diffraction grating grid, a first lens, an encoding pattern element, and a second lens, and
wherein an X-axis focal length of each of the lenses is twice a Y-axis focal length of that lens.

3. An illumination system comprising:
a light source to generate a light beam; and
a spatial encoding pattern generator comprising one or a plurality of optical elements to encode the light beam forming an imaging beam so as to concurrently illuminate an object by a plurality of different spatial encoding patterns, wherein each encoding pattern of said different encoding patterns is characterized by a distinct wavelength of the imaging pattern,
wherein said one or a plurality of optical elements to encode the imaging beam are aligned along an optical path in the following order: a diffraction grating grid, a first lens, an encoding pattern element, and a second lens, and
wherein said one or a plurality of optical elements to encode the imaging beam define the optical path comprising, in the following order, the diffraction grating grid, the first lens, the encoding pattern element, the second lens, a second diffraction grating grid, and a third lens.

4. The system of claim 3, wherein the first lens is distanced from the diffraction grating grid and from the encoding pattern element by a distance equal to an X-axis focal length of the first lens, wherein the second lens is distanced from the encoding pattern element by a distance equal to an X-axis focal length of the second lens, and wherein the third lens is distanced from the second diffraction grating grid by a distance equal to an X-axis focal length of the third lens.

5. The system of claim 4, wherein an X-axis focal length of each of the lenses is twice a Y-axis focal length of that lens.

6. An illumination system comprising:
a light source to generate a light beam; and
a spatial encoding pattern generator comprising one or a plurality of optical elements to encode the light beam forming an imaging beam so as to concurrently illuminate an object by a plurality of different spatial encoding patterns, wherein each encoding pattern of said different encoding patterns is characterized by a distinct wavelength of the imaging pattern,
wherein the illumination system is incorporated in an imaging system, the imaging system further comprising:
an imaging sensor for receiving the encoded imaging beam transmitted through the object or reflected off the object; and
a processor for decoding image data from the imaging and reconstructing an image of the object, and
wherein for reconstructing the image of the object the processor is configured to multiply an image of each encoding pattern of said different encoding patterns, that is obtained from the reflected or transmitted encoded imaging beam, by a corresponding decoding pattern to obtain a product and to sum all of the products to obtain the reconstructed image of the object.

7. A decoding system comprising:
an imaging sensor for receiving an encoded imaging beam that concurrently illuminated an object by a plurality of different spatial encoding patterns, wherein each encoding pattern of said different encoding patterns is characterized by a distinct wavelength of the imaging pattern, and that was transmitted through the object or reflected off the object; and
a processor for decoding image data from the imaging beam and reconstructing an image of the object, wherein, for reconstructing the image of the object, the processor is configured:
to multiply an image of each encoding pattern of said different encoding patterns, which image is obtained from the encoded imaging beam, by a corresponding decoding pattern to obtain a product, and
to sum all of the products to obtain the reconstructed image of the object.

8. An encoding method comprising:
generating a light beam; and
using a spatial encoding pattern generator, encoding the imaging beam so as to concurrently illuminate an object by a plurality of different spatial encoding patterns, wherein each encoding pattern of said different encoding patterns is characterized by a distinct wavelength of the imaging pattern,
wherein spatial encoding pattern generator comprises one or a plurality of optical elements to encode the imaging beam, which are aligned along an optical path in the following order: a diffraction grating grid, a first lens, an encoding pattern element, and a second lens, and
wherein the first lens is distanced from the diffraction grating grid and from the encoding pattern element by a distance equal to an X-axis focal length of the first lens, and wherein the second lens is distanced from the encoding pattern element by a distance equal to an X-axis focal length of the second lens.

9. An encoding method comprising:
generating a light beam; and
using a spatial encoding pattern generator, encoding the imaging beam so as to concurrently illuminate an object by a plurality of different spatial encoding patterns, wherein each encoding pattern of said different encoding patterns is characterized by a distinct wavelength of the imaging pattern,
wherein spatial encoding pattern generator comprises one or a plurality of optical elements to encode the imaging beam, which are aligned along an optical path in the following order: a diffraction grating grid, a first lens, an encoding pattern element, and a second lens, and
wherein an X-axis focal length of each of the lenses is twice a Y-axis focal length of that lens.

10. An encoding method comprising:
generating a light beam; and
using a spatial encoding pattern generator, encoding the imaging beam so as to concurrently illuminate an object by a plurality of different spatial encoding patterns, wherein each encoding pattern of said different encoding patterns is characterized by a distinct wavelength of the imaging pattern, wherein spatial encoding pattern generator comprises one or a plurality of optical elements to encode the imaging beam, which are aligned along an optical path in the following order: a diffraction grating grid, a first lens, an encoding pattern element, and a second lens, and wherein said one or a plurality of optical elements to encode the imaging beam define the optical path comprising, in the following order, the diffraction grating grid, the first lens, the encoding pattern element, the second lens, a second diffraction grating grid, and a third lens.

11. The method of claim 10, wherein the first lens is distanced from the diffraction grating grid and from the encoding pattern element by a distance equal to an X-axis focal length of the first lens, wherein the second lens is distanced from the encoding pattern element by a distance equal to an X-axis focal length of the second lens, and wherein the third lens is distanced from the second diffraction grating grid by a distance equal to an X-axis focal length of the third lens.

12. The method of claim 11, wherein an X-axis focal length of each of the lenses is twice a Y-axis focal length of that lens.

13. The method of claim 10, further comprising:

using an imaging sensor receiving the encoded imaging beam transmitted through the object or reflected off the object, and using a processor, decoding image data from the imaging and reconstructing an image of the object, and for reconstructing the image of the object, multiplying an image of each encoding pattern of said different encoding patterns, that is obtained from the reflected or transmitted encoded imaging beam, by a corresponding decoding pattern to obtain a product and summing all of the products to obtain the reconstructed image of the object.

14. A method comprising:

using an imaging sensor, receiving an encoded imaging beam that concurrently illuminated an object by a plurality of different spatial encoding patterns, wherein each encoding pattern of said different encoding patterns is characterized by a distinct wavelength of the imaging pattern, and that was transmitted through the object or reflected off the object; and using a processor, decoding image data from the imaging and reconstructing an image of the object, wherein reconstructing the image of the object comprises multiplying an image of each encoding pattern of said different encoding patterns, that is obtained from the reflected or transmitted encoded imaging beam, by a corresponding decoding pattern to obtain a product and to summing all of the products to obtain the reconstructed image of the object.

15. A method for imaging an object through a scattering medium, the method comprising:

using a light source, generating a light beam;

using a spatial encoding pattern generator that includes one or a plurality of optical elements, encoding the light beam to form an imaging beam so as to concurrently illuminate the object by a plurality of different spatial encoding patterns, wherein each encoding pattern of said different encoding patterns is characterized by a distinct wavelength of the imaging pattern;

combining the reference beam and the imaging beam into a combined beam, after the imaging beam was transmitted through the object or reflected off the object;

using an imaging sensor, receiving the combined beam; and using a processor, decoding image data from the combined beam and reconstructing an image of the object, wherein the reconstructing of the image comprises multiplying an image of each encoding pattern of said different encoding patterns, by a corresponding decoding pattern to obtain a product and to sum all of the products to obtain the reconstructed image of the object.

16. A system for imaging through a scattering medium, the system comprising:

a light source to generate a light beam; and a spatial encoding pattern generator comprising one or a plurality of optical elements to split the light beam to an imaging beam and a reference beam and to encode the imaging beam so as to concurrently illuminate an object by a plurality of different spatial encoding patterns, wherein each encoding pattern of said different encoding patterns is characterized by a distinct wavelength of the imaging pattern, and to combine the reference beam and the imaging beam into a combined beam, after the imaging beam was transmitted through the object or reflected off the object; and an imaging sensor for receiving the combined beam; and a processor for decoding image data from the combined beam and reconstructing an image of the object, wherein for reconstructing the image of the object the processor is configured to multiply an image of each encoding pattern of said different encoding patterns, that is obtained from the combined beam, by a corresponding decoding pattern to obtain a product and to sum all of the products to obtain the reconstructed image of the object.

* * * * *